(12) United States Patent
Wen

(10) Patent No.: US 11,149,061 B2
(45) Date of Patent: Oct. 19, 2021

(54) METHODS FOR PURIFYING AND/OR PRODUCING ANTI-FREEZE PROTEINS

(71) Applicant: Xin Wen, Alhambra, CA (US)

(72) Inventor: Xin Wen, Alhambra, CA (US)

(73) Assignees: The Board of Trustees of the California State University, Long Beach, CA (US); California State University, Los Angeles, Los Angeles, CA (US)

( * ) Notice: Subject to any disclaimer, the term of this patent is extended or adjusted under 35 U.S.C. 154(b) by 0 days.

(21) Appl. No.: 16/729,025

(22) Filed: Dec. 27, 2019

(65) Prior Publication Data
US 2020/0207808 A1    Jul. 2, 2020

Related U.S. Application Data

(60) Provisional application No. 62/787,693, filed on Jan. 2, 2019.

(51) Int. Cl.
| C07K 1/00 | (2006.01) |
| C07K 1/36 | (2006.01) |
| C07K 14/195 | (2006.01) |
| C07K 1/02 | (2006.01) |

(52) U.S. Cl.
CPC .................. C07K 1/36 (2013.01); C07K 1/02 (2013.01); C07K 14/195 (2013.01)

(58) Field of Classification Search
CPC ........... C07K 14/195; C07K 1/02; C07K 1/36
See application file for complete search history.

(56) References Cited

U.S. PATENT DOCUMENTS

| 2013/0165626 A1* | 6/2013 | Fukuoka | ................. C09K 3/185 |
| | | | 530/324 |
| 2014/0193854 A1* | 7/2014 | Kim | ..................... C12N 15/815 |
| | | | 435/69.1 |

FOREIGN PATENT DOCUMENTS

| EP | 1344827 A2 * | 9/2003 | ........... C07K 14/375 |
| EP | 1452539 A1 * | 9/2004 | ................ A23G 9/32 |

OTHER PUBLICATIONS

Munoz et al. Structure and application of antifreeze proteins from Antarctic bacteria. 2017. Microb Cell Fact (2017) 16:138 (Year: 2017).*

Halwani et al. Recombinant Dendroides canadensis antifreeze proteins as potential ingredients in cryopreservation solutions. Cryobiology, 2014; 68(3): 411-418 (Year: 2014).*

Chae et al. Purification and characterization of tenecin 4, a new anti-Gram-negative bacterial peptide, from the beetle *Tenebrio molitor.* Developmental and Comparative Immunology 36 (2012) 540-546 (Year: 2012).*

Natapol Amornwittawat et al.; "Polycarboxylates Enhance Beetle Antifreeze Protein Activity"; Biochim. Biophys. Acta; 2008; pp. 1942-1948; Elsevier B.V.

Sen Wang et al.; "Arginine, a Key Residue for the Enhancing Ability of an Antifreeze Protein of the Beetle *Dendroides canadensis*"; Biochemistry 2009, vol. 48; pp. 9696-9703; American Chemical Society.

Sen Wang et al.; "Expanding the Molecular Recognition Repertoire of Antifreeze Polypeptides: Effects on Nucleoside Crystal Growth"; Chem. Commun., 2012, vol. 48; pp. 11555-11557; The Royal Society of Chemistry 2012.

Sen Wang et al.; "Molecular Recognition of Methyl $\alpha$-$^D$-Mannopyranoside by Antifreeze (Glyco)Proteins"; Journal of the American Chemical Society, 2014, vol. 136; pp. 8973-8981; American Chemical Society.

Celeste Rodriguez et al.; "A Beetle Antifreeze Protein Protects Lactate Dehydrogenase Under Freeze-Thawing"; International Journal of Biological Macromolecules, vol. 136, 2019; pp. 1153-1160; Elsevier B.V.

Cathy A. Andorfer et al.; "Isolation and Characterization of cDNA Clones Encoding Antifreeze Proteins of the Pyrochroid Beetle *Dendroides canadensis*"; Journal of Insect Physiology, vol. 46, 2000; pp. 365-372; Elsevier Science Ltd.

Yih-Cherng Liou et al.; "A Complex Family of Highly Heterogeneous and Internally Repetitive Hyperactive Antifreeze Proteins from the Beetle *Tenebrio molitor*"; Biochemistry, 1999, vol. 38; pp. 11415-11424; American Chemical Society.

Ning Li et al.; "Enhancement of Insect Antifreeze Protein Activity by Solutes of Low Molecular Mass"; The Journal of Experimental Biology, vol. 201, 1998; pp. 2243-2251; The Company of Biologists Limited 1998; Cambridge, UK.

Lei Wang et al.; "Antifreeze Proteins of the Beetle *Dendroides canadensis* Enhance One Another's Activities"; Biochemistry 2005, vol. 44; pp. 10305-10312; American Chemical Society.

Michael J. Kuiper et al.; "Purification of Antifreeze Proteins by Adsorption to Ice"; Biochemical and Biophysical Research Communications, vol. 300, 2003; pp. 645-648; Elsevier Science (USA).

(Continued)

*Primary Examiner* — James H Alstrum-Acevedo
*Assistant Examiner* — Mercy H Sabila
(74) *Attorney, Agent, or Firm* — Andrew D. Fortney; Central California IP Group, P.C.

(57) ABSTRACT

A method of purifying an antifreeze protein (AFP) and methods of producing AFPs are disclosed. The method of purifying an AFP includes heating a crude AFP in an aqueous medium to a temperature and for a length of time sufficient to precipitate at least some thermally unstable proteins in the crude AFP and form a precipitate and a supernatant; and removing the precipitate from the supernatant. One method of producing an AFP includes collecting a crude source of the AFP; and purifying the AFP by the purification method. Another method of producing an AFP includes growing or culturing a host configured to express a recombinant AFP in a growth medium, and collecting a crude AFP from the host and/or the growth medium. The growth medium comprises water, a protein hydrolysate or other source of amino acids, a yeast extract, a biologically metabolizable $C_3$-$C_6$ polyol, and one or more phosphate salts.

20 Claims, 2 Drawing Sheets
Specification includes a Sequence Listing.

(56) References Cited

OTHER PUBLICATIONS

Mathieu Leclère et al.; "C-Linked Antifreeze Glycoprotein (C-AFGP) Analogues as Novel Cryoprotectants"; Bioconjugate Chemistry, 2011, vol. 22; pp. 1804-1810; American Chemical Society.

Dennis S. Friis et al.; "Low Thermodynamic but High Kinetic Stability of an Antifreeze Protein from Rhagium mordax"; Protein Science, 2014, vol. 23; pp. 760-768; Wiley-Blackwell, The Protein Society.

Daniel E. Mitchell et al.; "Antifreeze Protein Mimetic Metallohelices with Potent Ice Recrystallization Inhibition Activity"; The Journal of the American Chemical Society, 2017, vol. 139; pp. 9835-9838; ACS Publications.

Chris Sidebottom et al.; "Heat-Stable Antifreeze Protein from Grass"; Nature, vol. 406, Jul. 20, 2000; p. 256; Macmillan Magazines Ltd.

Roger Y. Tam et al.; "Solution Conformation of C-Linked Antifreeze Glycoprotein Analogues and Modulation of Ice Recrystallization"; J. Am. Chem. Soc., 2009, vol. 131; pp. 15745-15753; American Chemical Society.

Maya Bar et al.; "Efficient Production of a Folded and Functional, Highly Disulfide-Bonded β-helix Antifreeze Protein in Bacteria"; Protein Expression and Purification; vol. 48, 2006; pp. 243-252; Elsevier Inc.

Michael G. Tyshenko et al.; "Challenges in the Expression of Disulfide Bonded, Threonine-rich Antifreeze Proteins in Bacteria and Yeast"; Protein Expression and Purification; vol. 47, 2006; pp. 152-161; Elsevier Inc.

Cuan-Mei Yeh et al.; "Production of a Recombinant Type 1 Antifreeze Protein Analogue by *L. lactis* and Its Applications on Frozen Meat and Frozen Dough"; Journal of Agricultural and Food Chemistry; 2009, vol. 57; pp. 6216-6223; American Chemical Society.

\* cited by examiner

SEQUENCE LISTING

```
<160> NUMBER OF SEQ ID NOS: 22

<210> SEQ ID NO 1
<211> LENGTH: 83
<212> TYPE: PRT
<213> ORGANISM: Dendroides canadensis

<400> SEQUENCE: 1

Asn Cys Thr Gly Gly Ser Asp Cys Arg Ser Cys Thr Val Ser Cys Thr
1               5                   10                  15

Asp Cys Gln Asn Cys Pro Asn Ala Arg Thr Ala Cys Thr Arg Ser Ser
            20                  25                  30

Asn Cys Ile Asn Ala Leu Thr Cys Thr Asp Ser Tyr Asp Cys His Asn
        35                  40                  45

Ala Glu Thr Cys Thr Arg Ser Thr Asn Cys Tyr Lys Ala Lys Thr Cys
```

```
                     50                  55                  60
Thr Gly Ser Thr Asn Cys Tyr Glu Ala Thr Ala Cys Thr Asp Ser Thr
 65                  70                  75                  80

Gly Cys Pro

<210> SEQ ID NO 2
<211> LENGTH: 84
<212> TYPE: PRT
<213> ORGANISM: Dendroides canadensis

<400> SEQUENCE: 2

Gln Cys Thr Gly Gly Ser Asp Cys Arg Ser Cys Thr Val Ser Cys Thr
 1               5                  10                  15

Asp Cys Gln Asn Cys Pro Asn Ala Arg Thr Ala Cys Thr Arg Ser Ser
                 20                  25                  30

Asn Cys Asn Asn Ala Leu Thr Cys Thr Asp Ser Tyr Asp Cys His Asn
             35                  40                  45

Ala Glu Thr Cys Thr Arg Ser Thr Asn Cys Tyr Lys Ala Lys Thr Cys
         50                  55                  60

Thr Gly Ser Thr Asn Cys Tyr Glu Ala Thr Ala Cys Thr Asp Ser
 65                  70                  75                  80

Thr Gly Cys Pro

<210> SEQ ID NO 3
<211> LENGTH: 71
<212> TYPE: PRT
<213> ORGANISM: Dendroides canadensis

<400> SEQUENCE: 3

Gln Cys Thr Gly Gly Ser Asp Cys Gln Ser Cys Thr Val Ser Cys Thr
 1               5                  10                  15

Asp Cys Gln Asn Cys Pro Asn Ala Arg Thr Ala Cys Thr Gly Ser Ser
                 20                  25                  30

Asn Cys Ile Asn Ala Leu Thr Cys Thr Asp Ser His Asp Cys His Asn
             35                  40                  45

Ala Glu Thr Cys Thr Arg Ser Thr Asn Cys Tyr Lys Ala Lys Thr Cys
         50                  55                  60

Thr Asp Ser Thr Gly Cys Pro
 65                  70

<210> SEQ ID NO 4
<211> LENGTH: 71
<212> TYPE: PRT
<213> ORGANISM: Dendroides canadensis

<400> SEQUENCE: 4

Gln Cys Thr Gly Gly Ser Asp Cys Ser Ser Cys Thr Val Ser Cys Thr
 1               5                  10                  15

Asn Cys Gln Asn Cys Pro Asn Ala Arg Val Ala Cys Thr Gly Ser Thr
                 20                  25                  30

Asn Cys Ile Asn Ala Leu Thr Cys Thr Asp Ser His Asp Cys His Asn
             35                  40                  45

Ala Glu Thr Cys Thr Arg Ser Thr Asn Cys Tyr Lys Ala Lys Thr Cys
         50                  55                  60

Thr Asp Ser Thr Gly Cys Pro
 65                  70
```

<210> SEQ ID NO 5
<211> LENGTH: 104
<212> TYPE: PRT
<213> ORGANISM: Dendroides canadensis

<400> SEQUENCE: 5

Met Val Cys Gln Asn Leu Leu Leu Ile Ile Ser Val Val Leu Met Ser
1               5                   10                  15

Cys Leu Cys His Glu Tyr Tyr Ala Gln Cys Thr Gly Ala Pro Asp Cys
            20                  25                  30

Ser Ala Cys Thr Thr Ala Cys Thr Asp Cys Val Asn Cys Pro Asn Ala
        35                  40                  45

Leu Thr Ala Cys Thr Arg Ser Thr Asn Cys Tyr Lys Ala Val Thr Cys
    50                  55                  60

Thr Lys Ser Tyr Asp Cys Tyr Lys Ala Val Thr Cys Thr Asp Ser Thr
65                  70                  75                  80

Asn Cys Tyr Glu Ala Thr Ala Cys Thr Asn Ser Thr Gly Cys Pro Pro
                85                  90                  95

Ser Ala Tyr Ile His Gln Ile Asn
            100

<210> SEQ ID NO 6
<211> LENGTH: 122
<212> TYPE: PRT
<213> ORGANISM: Dendroides canadensis

<400> SEQUENCE: 6

Ser Ser Val Pro Ser Asn Ser Leu Leu Ile Ile Ser Val Val Leu Met
1               5                   10                  15

Cys Leu Cys His Glu Tyr Tyr Ala Val Cys Thr Gly Gly Pro Asn Cys
            20                  25                  30

Asn Ala Cys Thr Thr Ala Cys Thr Asn Cys Ile Asn Cys Pro Asn Ala
        35                  40                  45

Leu Leu Ala Cys Thr Asp Ser Thr Asn Cys Leu Lys Ala Val Thr Cys
    50                  55                  60

Thr Arg Ser Thr Lys Cys Asn Lys Ala Val Thr Cys Thr Asn Ser Ser
65                  70                  75                  80

Asp Cys Phe Lys Ala Val Thr Cys Thr Gly Ser Thr Asn Cys Tyr Lys
                85                  90                  95

Ala Lys Ser Cys Ala Ala Ser Thr Asn Cys Phe Glu Ala Thr Thr Ser
            100                 105                 110

Cys Val Asn Ser Thr Gly Cys Pro Pro Pro
            115                 120

<210> SEQ ID NO 7
<211> LENGTH: 121
<212> TYPE: PRT
<213> ORGANISM: Dendroides canadensis

<400> SEQUENCE: 7

Met Val Trp Val Cys Lys Ser Ser Leu Leu Ile Ile Ser Val Val Leu
1               5                   10                  15

Met Cys Lys Tyr Asp Glu Cys His Ser Gln Cys Thr Gly Gly Ser Asp
            20                  25                  30

Cys Ser Ser Cys Thr Gly Ala Cys Thr Thr Cys Arg Asn Cys Pro Asn
        35                  40                  45

Ala Met Thr Ala Cys Thr Gly Ser Thr Gly Cys Tyr Arg Ala Thr Thr
    50                  55                  60

Cys Thr Arg Ser Ser Glu Cys Asn Asn Ala Val Thr Cys Thr Gly Ser
65                  70                  75                  80

Tyr Asp Cys Tyr Asn Ala Ala Thr Cys Thr Gly Ser Thr Asn Cys Tyr
                85                  90                  95

Lys Ala Thr Thr Cys Thr Gly Ser Thr Asn Cys Tyr Glu Ala Thr Thr
            100                 105                 110

Ala Cys Thr Asp Ser Thr Gly Cys Pro
        115                 120

<210> SEQ ID NO 8
<211> LENGTH: 148
<212> TYPE: PRT
<213> ORGANISM: Dendroides canadensis

<400> SEQUENCE: 8

Met Val Trp Val Cys Lys Ser Ser Trp Leu Ile Ile Gly Val Val Leu
1               5                   10                  15

Met Cys Lys Tyr Asp Glu Cys His Ser Glu Cys Thr Gly Gly Ser Asp
                20                  25                  30

Cys Arg Ser Cys Thr Ala Ala Cys Thr Ser Cys Gln Asn Cys Pro Asn
            35                  40                  45

Ala Arg Ser Ala Cys Thr Gly Ser Thr Val Cys His Lys Ala Gln Thr
        50                  55                  60

Cys Thr Gly Ser Thr Gly Cys Tyr Asn Ala Met Thr Cys Thr Arg Ser
65                  70                  75                  80

Ser Glu Cys Asn Asn Ala Gln Thr Cys Thr Gly Ser His Asp Cys His
                85                  90                  95

Asn Ala Gln Thr Cys Thr Gly Ser Tyr Asp Cys Tyr Asn Ala Thr Thr
            100                 105                 110

Cys Thr Gly Ser Thr Asn Cys Tyr Arg Ala Thr Thr Cys Thr Gly Ser
        115                 120                 125

Thr Asn Cys His Arg Ala Thr Ala Cys Thr Gly Ser Thr Gly Cys Pro
    130                 135                 140

Gly Ser Gly Ala
145

<210> SEQ ID NO 9
<211> LENGTH: 98
<212> TYPE: PRT
<213> ORGANISM: Dendroides canadensis

<400> SEQUENCE: 9

Arg Ala Arg Tyr Leu Gly Leu Gln Ser Ser Leu Leu Val Ile Ser Val
1               5                   10                  15

Val Leu Met Phe Val Cys His Glu Cys Tyr Gly Gln Cys Thr Gly Gly
                20                  25                  30

Ser Asp Cys Gln Ser Cys Thr Val Ser Cys Thr Asp Cys Gln Asn Cys
            35                  40                  45

Pro Asn Ala Arg Thr Ala Cys Thr Gly Ser Ser Asn Cys Ile Asn Ala
        50                  55                  60

Leu Thr Cys Thr Asp Ser His Asp Cys His Asn Ala Glu Thr Cys Thr
65                  70                  75                  80

Arg Ser Thr Asn Cys Tyr Lys Ala Lys Thr Cys Thr Asp Ser Thr Gly
                85                  90                  95

Cys Pro

<210> SEQ ID NO 10
<211> LENGTH: 84
<212> TYPE: PRT
<213> ORGANISM: Tenebrio molitor

<400> SEQUENCE: 10

Gln Cys Thr Gly Ala Ala Asp Cys Thr Ser Cys Thr Ala Ala Cys Thr
1               5                   10                  15

Gly Cys Gly Asn Cys Pro Asn Ala Val Thr Cys Thr Asn Ser Gln His
            20                  25                  30

Cys Val Lys Ala Thr Thr Cys Thr Gly Ser Thr Asp Cys Asn Thr Ala
        35                  40                  45

Val Thr Cys Thr Asn Ser Lys Asp Cys Phe Glu Ala Gln Thr Cys Thr
50                  55                  60

Asp Ser Thr Asn Cys Tyr Lys Ala Thr Ala Cys Thr Asn Ser Thr Gly
65                  70                  75                  80

Cys Pro Gly His

<210> SEQ ID NO 11
<211> LENGTH: 84
<212> TYPE: PRT
<213> ORGANISM: Tenebrio molitor

<400> SEQUENCE: 11

Gln Cys Thr Gly Gly Ala Asp Cys Thr Ser Cys Thr Gly Ala Cys Thr
1               5                   10                  15

Gly Cys Gly Asn Cys Pro Asn Ala Val Thr Cys Thr Asn Ser Gln His
            20                  25                  30

Cys Val Lys Ala Asn Thr Cys Thr Gly Ser Thr Asp Cys Asn Thr Ala
        35                  40                  45

Gln Thr Cys Thr Asn Ser Lys Asp Cys Phe Glu Ala Asn Thr Cys Thr
50                  55                  60

Asp Ser Thr Asn Cys Tyr Lys Ala Thr Ala Cys Thr Asn Ser Thr Gly
65                  70                  75                  80

Cys Pro Gly His

<210> SEQ ID NO 12
<211> LENGTH: 120
<212> TYPE: PRT
<213> ORGANISM: Microdera punctipennis

<400> SEQUENCE: 12

Met Ala Leu Thr Thr Lys Trp Phe Leu Ile Ala Val Val Met Cys
1               5                   10                  15

Leu Cys Ser Glu Tyr Tyr Cys Gln Cys Thr Gly Gly Ser Asp Cys Thr
            20                  25                  30

Ser Cys Thr Ala Ala Cys Thr Asn Cys Gln Asn Cys Pro Asn Ala Gln
        35                  40                  45

Thr Cys Thr Asn Ser Lys Asn Cys Lys Asn Ala Gln Thr Cys Thr Asp
50                  55                  60

Ser Thr Asn Cys Lys Asn Ala Gln Thr Cys Thr Gly Ser Tyr Asn Cys
65                  70                  75                  80

Asn Arg Ala Met Thr Cys Thr Asn Ser Tyr Asp Cys Phe Glu Ala Ala
                85                  90                  95

Thr Cys Thr Asp Ser Thr Asn Cys Tyr Lys Ala Thr Ala Cys Thr His
                100                 105                 110

```
Ser Thr Gly Cys Pro Asn Lys Gly
        115                 120
```

```
<210> SEQ ID NO 13
<211> LENGTH: 93
<212> TYPE: PRT
<213> ORGANISM: Microdera punctipennis

<400> SEQUENCE: 13

Met Ala Leu Thr Thr Lys Trp Phe Leu Ile Ala Val Val Met Cys
1               5                   10                  15

Leu Cys Ser Glu Tyr Tyr Cys Gln Cys Thr Gly Gly Ser Asp Cys Thr
                20                  25                  30

Ser Cys Thr Ala Ala Cys Thr Asn Cys Gln Asn Cys Pro Asn Ala Gln
            35                  40                  45

Thr Cys Thr Asp Ser Gly Asn Cys Lys Asn Ala Gln Thr Cys Thr Gly
        50                  55                  60

Ser Thr Asn Cys Asn Arg Ala Met Thr Cys Thr Asn Ser Tyr Asp Cys
65                  70                  75                  80

Phe Glu Ala Val Thr Leu Thr Phe Ile Trp Thr Ser Cys
                85                  90
```

```
<210> SEQ ID NO 14
<211> LENGTH: 134
<212> TYPE: PRT
<213> ORGANISM: Rhagium inquisitor

<400> SEQUENCE: 14

Cys Arg Ala Val Gly Val Asp Gly Arg Ala Val Thr Asp Ile Gln Gly
1               5                   10                  15

Thr Cys His Ala Lys Ala Thr Gly Ala Gly Ala Met Ala Ser Gly Thr
                20                  25                  30

Ser Glu Pro Gly Ser Thr Ser Thr Ala Thr Ala Thr Gly Arg Gly Ala
            35                  40                  45

Thr Ala Arg Ser Thr Ser Thr Gly Arg Gly Thr Ala Thr Thr Thr Ala
        50                  55                  60

Thr Gly Thr Ala Ser Ala Thr Ser Asn Ala Ile Gly Gln Gly Thr Ala
65                  70                  75                  80

Thr Thr Thr Ala Thr Gly Ser Ala Gly Gly Arg Ala Thr Gly Ser Ala
                85                  90                  95

Thr Thr Ser Ser Ser Ala Ser Gln Pro Thr Gln Thr Gln Thr Ile Thr
                100                 105                 110

Gly Pro Gly Phe Gln Thr Ala Lys Ser Phe Ala Arg Asn Thr Ala Thr
            115                 120                 125

Thr Thr Val Thr Ala Ser
        130
```

```
<210> SEQ ID NO 15
<211> LENGTH: 143
<212> TYPE: PRT
<213> ORGANISM: Rhagium inquisitor

<400> SEQUENCE: 15

Gly Tyr Ser Cys Arg Ala Val Gly Val Asp Gly Arg Ala Val Thr Asp
1               5                   10                  15

Ile Gln Gly Thr Cys His Ala Lys Ala Thr Gly Ala Gly Ala Met Ala
                20                  25                  30

Ser Gly Thr Ser Glu Pro Gly Ser Thr Ser Thr Ala Thr Ala Thr Gly
```

```
                35                  40                  45
Arg Gly Ala Thr Ala Arg Ser Thr Ser Thr Gly Arg Gly Thr Ala Thr
             50                  55                  60
Thr Thr Ala Thr Gly Thr Ala Ser Ala Thr Ser Asn Ala Ile Gly Gln
 65                  70                  75                  80
Gly Thr Ala Thr Thr Ala Thr Gly Ser Ala Gly Gly Arg Ala Thr
                 85                  90                  95
Gly Ser Ala Thr Thr Ser Ser Ser Ala Ser Gln Pro Thr Gln Thr Gln
                100                 105                 110
Thr Ile Thr Gly Pro Gly Phe Gln Thr Ala Lys Ser Phe Ala Arg Asn
                115                 120                 125
Thr Ala Thr Thr Thr Val Thr Ala Ser His His His His His His
            130                 135                 140

<210> SEQ ID NO 16
<211> LENGTH: 82
<212> TYPE: PRT
<213> ORGANISM: Pseudopleuronectes americanus

<400> SEQUENCE: 16

Met Ala Leu Ser Leu Phe Thr Val Gly Gln Leu Ile Phe Leu Phe Trp
 1               5                  10                  15
Thr Met Arg Ile Thr Glu Ala Ser Pro Asp Pro Ala Ala Lys Ala Ala
                20                  25                  30
Pro Ala Ala Ala Ala Pro Ala Ala Ala Pro Asp Thr Ala Ser
                35                  40                  45
Asp Ala Ala Ala Ala Ala Leu Thr Ala Ala Asn Ala Lys Ala Ala
             50                  55                  60
Ala Glu Leu Thr Ala Ala Asn Ala Lys Ala Ala Ala Ala Ala Thr Ala
 65                  70                  75                  80
Arg Gly

<210> SEQ ID NO 17
<211> LENGTH: 129
<212> TYPE: PRT
<213> ORGANISM: Hemitripterus americanus

<400> SEQUENCE: 17

Gln Arg Ala Gly Pro Asn Cys Pro Ala Gly Trp Gln Pro Leu Gly Asp
 1               5                  10                  15
Arg Cys Ile Tyr Tyr Glu Thr Thr Ala Met Thr Trp Ala Leu Ala Glu
                20                  25                  30
Thr Asn Cys Met Lys Leu Gly Gly His Leu Ala Ser Ile His Ser Gln
                35                  40                  45
Glu Glu His Ser Phe Ile Gln Thr Leu Asn Ala Gly Val Val Trp Ile
             50                  55                  60
Gly Gly Ser Ala Cys Leu Gln Ala Gly Ala Trp Thr Trp Ser Asp Gly
 65                  70                  75                  80
Thr Pro Met Asn Phe Arg Ser Trp Cys Ser Thr Lys Pro Asp Asp Val
                85                  90                  95
Leu Ala Ala Cys Cys Met Gln Met Thr Ala Ala Ala Asp Gln Cys Trp
                100                 105                 110
Asp Asp Leu Pro Cys Pro Ala Ser His Lys Ser Val Cys Ala Met Thr
                115                 120                 125
Phe
```

<210> SEQ ID NO 18
<211> LENGTH: 70
<212> TYPE: PRT
<213> ORGANISM: Zoarces americanus

<400> SEQUENCE: 18

Ala Ala Gln Ala Ser Val Val Ala Asn Gln Leu Ile Pro Ile Asn Thr
1               5                   10                  15

Ala Leu Thr Leu Val Met Met Arg Ser Glu Val Val Thr Pro Val Gly
            20                  25                  30

Ile Pro Ala Glu Asp Ile Pro Arg Leu Val Ser Met Gln Val Asn Arg
        35                  40                  45

Ala Val Pro Leu Gly Thr Thr Leu Met Pro Asp Met Val Lys Gly Tyr
    50                  55                  60

Ala Ala Lys Asp Glu Leu
65                  70

<210> SEQ ID NO 19
<211> LENGTH: 66
<212> TYPE: PRT
<213> ORGANISM: Zoarces americanus

<400> SEQUENCE: 19

Met Asn Gln Ala Ser Val Val Ala Asn Gln Leu Ile Pro Ile Asn Thr
1               5                   10                  15

Ala Leu Thr Leu Val Met Met Arg Ser Glu Val Val Thr Pro Val Gly
            20                  25                  30

Ile Pro Ala Glu Asp Ile Pro Arg Leu Val Ser Met Gln Val Asn Arg
        35                  40                  45

Ala Val Pro Leu Gly Thr Thr Leu Met Pro Asp Met Val Lys Gly Tyr
    50                  55                  60

Ala Ala
65

<210> SEQ ID NO 20
<211> LENGTH: 168
<212> TYPE: PRT
<213> ORGANISM: Brachyopsis segaliensis

<400> SEQUENCE: 20

Met Leu Thr Val Ser Leu Leu Val Cys Ala Met Met Ala Leu Thr Gln
1               5                   10                  15

Ala Asp His Asp Gly Val Leu Lys Gly Thr Ala Thr Glu Ala Gly Glu
            20                  25                  30

Val Ser Pro Val Phe Arg Ser Arg Arg Ala Leu Val Cys Pro Ala Gly
            35                  40                  45

Trp Thr Leu His Gly Gln Arg Cys Phe Tyr Ser Glu Ala Thr Ala Met
    50                  55                  60

Thr Trp Asp Leu Ala Glu Ala Asn Cys Val Asn Lys Gly Gly His Leu
65                  70                  75                  80

Ala Ser Ile His Ser Leu Glu Glu Gln Leu Tyr Ile Lys Asp Ile Val
                85                  90                  95

Ala Gly Ile Val Trp Ile Gly Gly Ser Ala Cys Lys Val Ala Gly Ala
            100                 105                 110

Trp Ser Trp Thr Asp Gly Thr Pro Val Asp Tyr Arg Thr Trp Cys Pro
        115                 120                 125

Thr Lys Pro Asn Asp Ile Leu Ser Asp Cys Cys Met Gln Met Thr Ala

```
                    130                 135                 140
Ala Val Asp Lys Cys Trp Asp Leu Pro Cys Pro Ala Ser His Ala
145                 150                 155                 160

Ser Ile Cys Ala Lys Ala Ala Ile
                165

<210> SEQ ID NO 21
<211> LENGTH: 133
<212> TYPE: PRT
<213> ORGANISM: Lolium perenne

<400> SEQUENCE: 21

Met Asp Glu Gln Pro Asn Thr Ile Ser Gly Ser Asn Asn Thr Val Arg
1               5                   10                  15

Ser Gly Ser Lys Asn Val Leu Ala Gly Asn Asp Asn Thr Val Ile Ser
            20                  25                  30

Gly Asp Asn Ser Val Ser Gly Ser Asn Asn Thr Val Val Ser Gly
        35                  40                  45

Asn Asp Asn Thr Val Thr Gly Ser Asn His Val Val Ser Gly Thr Asn
    50                  55                  60

His Ile Val Thr Asp Asn Asn Asn Val Ser Gly Asn Asp Asn Asn
65                  70                  75                  80

Val Ser Gly Ser Phe His Thr Val Ser Gly Gly His Asn Thr Val Ser
                85                  90                  95

Gly Ser Asn Asn Thr Val Ser Gly Ser Asn His Val Val Ser Gly Ser
            100                 105                 110

Asn Lys Val Val Thr Asp Ala Ala Lys Leu Ala Ala Ala Leu Glu His
            115                 120                 125

His His His His His
        130

<210> SEQ ID NO 22
<211> LENGTH: 94
<212> TYPE: PRT
<213> ORGANISM: Sulfitobacter sp. D7

<400> SEQUENCE: 22

Met Thr Pro Phe Thr Phe Phe Ala Leu Gln Ser Gln Phe Ala Ala Leu
1               5                   10                  15

Ala Val Glu Thr Gln Ile Val Met Ser Leu Arg Leu Leu Ala Met Ala
            20                  25                  30

Gly Ala Leu Pro Ala Arg Pro Gly Glu Asn Asn Arg Met Val Ala Glu
            35                  40                  45

Lys Gly Pro Ala Met Val Lys Ala Phe Ser Ala Gly Thr Gln Ala Met
    50                  55                  60

Met Leu Gly Lys Ser Pro Asp Gln Val Met Asn Ala Ser Leu Ala Pro
65                  70                  75                  80

Leu Ala Arg Lys Val Arg Gln Asn Arg Lys Arg Leu Met Lys
                85                  90
```

METHODS FOR PURIFYING AND/OR PRODUCING ANTI-FREEZE PROTEINS

RELATED APPLICATION

This application claims the benefit of U.S. Provisional Pat. Appl. No. 62/787,693, filed Jan. 2, 2019, which is incorporated herein by reference in its entirety.

FEDERAL FUNDING STATEMENT

This work was supported by Grant Nos. NIH SC3GM086249, NSF 1840835 and NSF IIP1827782.

STATEMENT REGARDING FEDERAL SPONSORSHIP

The present invention was supported at least in part by National Science Foundation Grant Nos. NSF 1827782 and NSF 1840835.

SEQUENCE LISTING

The present application incorporates by reference a Sequence Listing in the ASCII text file identified by the file name "CSULA-011 SEQ LISTING 20200318_ST25.txt", created on Mar. 18, 2020, and having a size of 21,670 bytes.

FIELD OF THE INVENTION

The present invention generally relates to the field of anti-freeze proteins (AFPs). More specifically, embodiments of the present invention pertain to methods of producing and/or purifying AFPs.

DISCUSSION OF THE BACKGROUND

Antifreeze proteins (AFPs) are found in many organisms that need to survive in subfreezing environments, such as bacteria, fungi, fish, plants, and insects. AFPs lower the freezing point of aqueous solutions or suspensions such as blood without altering their melting point. Of all the organisms that transcribe AFPs, insects appear to exhibit the greatest antifreeze protein activity. Insect AFPs have a relatively high thermal hysteresis value (i.e., the difference between freezing and melting points).

Antifreeze proteins (AFPs) are a group of polypeptides naturally occurring in many cold-adapted organisms (e.g., freezing-avoidance and freezing-tolerant organisms) to allow them to survive at subzero temperatures. Some AFPs are glycoproteins, which are also called antifreeze glycoproteins (AFGPs). AF(G)Ps were first identified in polar fish, and have been found in diverse organisms including microorganisms (e.g., bacteria), plants, insects, and arthropods.

Although there are a variety of AF(G)P structures, they are characterized by their ability to bind to ice and inhibit or slow ice growth and/or ice recrystallization. Therefore, AF(G)Ps are also known as ice-binding proteins (IBP) or ice structuring proteins (ISP).

AFPs can depress the freezing point of water in a non-colligative manner, apparently without changing the melting point of water. The difference between the depressed freezing point and the (unchanged) melting point is termed thermal hysteresis (TH), and the value of TH is usually a measure of the antifreeze activity of AFPs.

AFPs have many industrial applications in food, agriculture, and other related industries. Moreover, new roles of AFPs in controlling the crystallization of industrially important compounds, as well as in protecting biologics under heat stresses, greatly expand the potential applications of AFPs. Purified AFPs are in great demand in research and various health and industrial applications.

AF(G)Ps often occur as a series of isoforms in a species without close similarities to any other known proteins and adopt diverse structures (e.g., a single α-helix, a helix bundle, a β-solenoid, a globular fold of mixed structure). For example, different types of fish AFPs have been characterized. Type I fish AFPs are small amphipathic α-helical proteins containing periodically repeating amino acids and their molecular weights are about 3-5 kDa. Type II and Type III fish AFPs are globular proteins without repeating units that consist of varied secondary structures. Their molecular weights are about 14-16 kDa and about 6 kDa, respectively. For another example, fish AFGPs mainly consist of repeat units of two or three amino acids, one of them glycosylated, usually with 4 to 32 repeat units and a molecular weight from 2 kDa to 34 kDa.

Mimetics of AF(G)Ps have been synthesized, and various engineered AF(G)Ps (e.g., recombinant AFPs, mutations), fragments of AF(G)Ps, active mimetic fragments of AF(G)Ps have been reported. Natural or engineered AF(G)Ps (e.g., mutations), active fragments of AF(G)Ps, mimetics of AF(G)Ps, their active mimetic fragments, and combinations thereof can also bind to ice crystals to inhibit or reduce growth and/or recrystallization of ice.

Some natural AF(G)Ps directly isolated from specific species have been reported to be very stable and remain active under extreme conditions (e.g., extreme temperatures and pH variations). For example, an AFP isolated from an overwintering perennial ryegrass, *Lolium perenne* (a plant AFP having less TH value than fish/insect AF(G)Ps, while having better ice recrystallization prevention properties), is stable at 100° C. (Sidebottom et al., *Nature* [2000] 405, 256). In another example, an AFP isoform from *Dendroides canadensis* (DAFP-4) is active after exposure to very wide temperature and pH ranges (see Li N, Andorfer C A, Duman J G (1998), "Enhancement of insect antifreeze protein activity by solutes of low molecular mass," *J. Exp. Biol.* 201:2243-2251). Generally, these AF(G)Ps can remain active at high temperatures (e.g., 30° C. above room temperature). There are other AF(G)Ps that denature after an exposure or repeated exposures at temperatures above room temperature (e.g., above 29° C.), but that can refold into their native state and regain activity after exposure to an even higher temperature (e.g., RmAFP1, a recombinant AFP from the beetle *Rhagium mordax*; see Friis et al., "Low thermodynamic but high kinetic stability of an antifreeze protein from *Rhagium mordax*," *Protein Science* 2014 vol. 23:760-768). However, AFPs that had already been purified were used in these tests of AF(G)P thermal behavior.

The applications of AFPs can reach diverse fields, such as food, pharmaceutical, medicine, agriculture industries (Chapman et al., "Frozen food products comprising antifreeze protein (AFP) type III HPLC 12," U.S. Pat. No. 6,914,043; Daniel et al., "Ice cream confection containing an antifreeze protein," European Pat. Publ. No. 14 17 892 A1). There is great potential for applying AFPs in various fields, such as foods and beverages, pharmaceuticals and biomedicines. For example, AFPs can improve the storage properties of perishable food and pharmaceutical products, as well as the quality of cells, tissues, and organs during cryopreservation. Furthermore, AFPs may have other uses in medicine.

Consequently, there is a need for a process capable of reliably providing relatively large amounts of purified AFPs.

AF(G)Ps in controlling the crystallization of non-ice-like compounds (ice-like compounds include ice and gas hydrates) have been reported recently (see, e.g., Xin Wen and Sen Wang, *Nucleoside crystals, crystal nucleation and growth control with antifreeze proteins*, U.S. Pat. No. 9,394, 327; *Chemical & Engineering News* (2014), Vol. 92, Iss. 26, p. 22; Wang et al., "Expanding the molecular recognition repertoire of antifreeze polypeptides: effects on nucleoside crystal growth," *Chem. Commun.* 48:11555-11557 [2012]). The correlation between the antifreeze activity of AFPs and their effects on controlling the crystallization of non-ice-like compounds have also been demonstrated (see, e.g., Wang, S. et al., "Molecular Recognition of Methyl α-D-Mannopyranoside by Antifreeze (Glyco)Proteins," *J. Am. Chem. Soc.* [2014], 136: 8973-8981). These new roles for AF(G)Ps greatly expand the applications of AF(G)Ps.

Many organisms produce a complex family of heterogeneous AFPs. The yellow mealworm, *Tenebrio molitor*, produces antifreeze proteins known as TmAFPs (e.g., one or more of 17 known isoforms of TmAFPs; see Liou Y. et al., "A Complex Family of Highly Heterogeneous and Internally Repetitive Hyperactive Antifreeze Proteins from the Beetle *Tenebrio molitor*," *Biochemistry* 1999, 38, 11415-11424). There are at least 13 known AFPs from *Dendroides canadensis* (DAFPs) containing varying numbers and sizes of repeat units with sizes of 7-17 kDa (Andorfer C A and Duman J G, "Isolation and characterization of cDNA clones encoding antifreeze proteins of the pyrochroid beetle *Dendroides canadensis*," *Journal of Insect Physiology* 46 [2000], 365-372).

Currently, the production of many AFPs are still from their original sources. For example, plant AFPs are usually isolated from plant seedlings, and insect AFP isoforms are generally prepared from the larvae. The steps for their production include collecting the species under specific conditions, extracting the crude resource of the proteins of interests, and performing a series of high-pressure liquid chromatography (HPLC) processes. The resulting AFPs may be obtained in limited amounts and/or in less-than-desired quality. In another example, commercially available fish AFPs, including Types I-III and AFGPs, are all purified from their natural sources (e.g., cold ocean teleost fish, see https://www.antifreezeprotein.com/product/) and certain types of AFPs are often not available.

Purifying AFPs includes the removal of other ingredients from the original source of the AFP or the impurities (e.g., other proteins, polysaccharides, cells debris) from the host cells (e.g., following expression/production of recombinant AFPs [rAFPs]). Furthermore, processes for recovering a target protein directly from a crude culture medium have been developed. For example, expanded bed adsorption (EBA) can purify some proteins without separate treatments for removing the cells, concentrating the medium, etc., after cell culture is complete.

Recombinant proteins produced in bacterial, yeast, plant, fungal and mammalian cells represent a major source of proteins used in various fields and industries, as well as in research and academia, because the production of recombinant proteins does not depend on the supply of a specific species. Consequently, rapid production of recombinant proteins with desired purity is crucial for the economical supply of recombinant proteins. Currently, in a laboratory setting, expression of recombinant AFPs generally takes more than two days. The existing methods of producing purified recombinant AFPs generally include at least two or three chromatography processes, which takes a great amount of time (usually at least 7-10 days) and requires large amounts of reagents. This significantly impedes the commercialization of recombinant AFPs.

This "Discussion of the Background" section is provided for background information only. The statements in this "Discussion of the Background" are not an admission that the subject matter disclosed in this "Discussion of the Background" section constitutes prior art to the present disclosure, and no part of this "Discussion of the Background" section may be used as an admission that any part of this application, including this "Discussion of the Background" section, constitutes prior art to the present disclosure.

SUMMARY OF THE INVENTION

Embodiments of the present invention pertain to methods of making, purifying and/or producing one or more antifreeze proteins (AFPs). The present invention provides a rapid and efficient method of producing highly purified AFPs. The method(s) described herein greatly reduce the time and costs of AFP manufacturing and purification. For example, the time for expression, production and/or purification of recombinant AFPs is reduced to within one day.

With the invention described herein, purified AFPs can be obtained using a reduced number of chromatographic processes, or even without using chromatography at all. The improvements provided by the invention described herein greatly reduce the production time (e.g., by more than 50%) and the cost (e.g., by more than 50%) of manufacturing/producing AFPs.

In one aspect, the present invention concerns a method of purifying an antifreeze protein (AFP), comprising heating a crude AFP in an aqueous medium to a temperature and for a length of time sufficient to precipitate at least some thermally unstable proteins in the crude AFP and form a precipitate and a supernatant; and removing the precipitate from the supernatant. In various embodiments, the temperature may be 45-90° C. (e.g., 60-75° C.), and the length of time may be from 2 min to 4 hours (e.g., 10 min-2 h).

The AFP may be selected from the group consisting of fish AFPs (e.g., type I AFPs, type II AFPs, type III AFPs, type IV AFPs), plant AFPs, insect AFPs, arthropod AFPs, bacteria AFPs, fungi AFPs, fish, plant and insect antifreeze glycoproteins (AFGPs), antifreeze polypeptides and peptides, active fragments of AFPs, AFGPs, antifreeze polypeptides and antifreeze peptides, mimetics of AFPs, AFGPs, antifreeze polypeptides and antifreeze peptides, active fragments of antifreeze protein, glycoprotein, polypeptide and peptide mimetics, and combinations, analogs and homologs thereof. The selected AFP is predominantly present in the organism in winter.

In other examples, the AFP may have an amino acid sequence of the formula $R^1$-(AA1-AA1-AA2)$_x$-$R^2$. Each AA1 is independently Ala, Asn, Gly, Val, Leu Pro, Phe, Thr, Tyr, or Ile, each AA2 is independently Thr or Ser or Tyr, $R^1$ is H, $C_{1-6}$ alkyl, $R^3$—C(=O)— or $R^3$—OC(=O)—, x is an integer of at least 3, $R^2$ is OH, $C_{1-6}$ alkoxy, $R^4$—NH— or $R^4{}_2$N—, $R^3$ is $C_{1-6}$ alkyl, $C_{6-10}$ aryl, or $C_{1-6}$ alkyl or $C_{6-10}$ aryl substituted with one or more halogen atoms and/or $C_{1-4}$ alkyl groups, and $R^4$ is $C_{1-4}$ alkyl. The AFP or AFGP (AF[G]P) may be natural, engineered, or synthesized.

The antifreeze protein, glycoprotein, polypeptide and peptide analogs may have (1) an amino acid sequence that differs from the amino acid sequence of the native protein, glycoprotein, polypeptide or peptide by a limited number of amino acids (e.g., the number may be 30% or less than the total number of amino acids in the sequence, such as from 5 to 30 amino acids) and (2) at least the same or similar (e.g., ≥50% of the) antifreeze activity and/or thermal stability as the native protein, glycoprotein, polypeptide or peptide. The antifreeze protein, glycoprotein, polypeptide and peptide analogs may also include those with the same amino acid sequence of the native protein, glycoprotein, polypeptide or peptide, but modified with non-amino acid substitutions and/or end groups (e.g., amide or ester groups on a carboxylic acid, carboxyl groups on an amine, thiol or alcohol, one or more alkyl groups on an amide, etc.). Antifreeze protein, glycoprotein, polypeptide and peptide analogs may also include those disclosed in U.S. Pat. No. 9,394,327, the relevant portions of which are incorporated herein by reference, and antifreeze peptoids and polymers such as those disclosed in International Pat. Publ. No. WO 2017/066454, Tam R. Y. et al., "Solution Conformation of C-Linked Antifreeze Glycoprotein Analogues and Modulation of Ice Recrystallization," *J. Am. Chem. Soc.* (2009), 131:43, 15745-15753, 139:29, 9835-9838, Leclere, M. et al., "C-Linked Antifreeze Glycoprotein (C-AFGP) Analogues as Novel Cryoprotectants" *Bioconjugate Chem.,* 2011, 22 (9), pp 1804-1810, Yeh, C-M, et al., "Production of a Recombinant Type 1 Antifreeze Protein Analogue by *L. lactis* and Its Applications on Frozen Meat and Frozen Dough," *J. Agric. Food Chem.* 2009, 57, 6216-6223, and in Mitchell, D. E., et al., "Antifreeze Protein Mimetic Metallohelices with Potent Ice Recrystallization Inhibition Activity," *J. Am. Chem. Soc.* (2017) 139:29, 9835-9838, the relevant portions of which are incorporated herein by reference.

The AFP may comprise an insect AFP such as a DAFP or TmAFP or an isoform or analog thereof having an amino acid sequence of the formula A-(Thr-X-Thr-Y)$_z$-B, where A is a sequence of at least 1 amino acid (e.g., 8-12 amino acids, such as Gln-Cys-Thr-Gly-Gly-Ser-Asp-Cys-Ser-Ser-Cys), X is a sequence of from 1 to 3 amino acids that may include Cys, Y is a sequence of 1-12 amino acids, z is an integer of from 3 to 32 (e.g., 3 to 8), and B is a sequence of 1-5 amino acids (e.g., Gly-Cys-Pro). For example, specific DAFPs include DAFP-1 (SEQ ID NO 1), DAFP-2 (SEQ ID NO 2), DAFP-4 (SEQ ID NO 3), DAFP-6 (SEQ ID NO 4), DAFP-3 (SEQ ID NO 5), DAFP-5 (SEQ ID NO 6), DAFP-8 (SEQ ID NO 7), DAFP-11 (SEQ ID NO 8), and DAFP-13 (SEQ ID NO 9). In other examples, specific TmAFPs include TmAFP isoform 1 (SEQ ID NO 10, which is a partial sequence of the full-length AFP) and TmAFP isoform 2 (SEQ ID NO 11, which is a partial sequence of the full-length AFP). A, X and Y may be derived from any of these DAFP and TmAFP sequences. In further examples, other insect AFPs include MpAFP isoform 1 (SEQ ID NO 12), MpAFP isoform 2 (SEQ ID NO 13), RiAFP isoform 1 (SEQ ID NO 14, which is a partial sequence of the full-length AFP), and RiAFP isoform 2 (SEQ ID NO 15). Some of the protein sequences in the Sequence Listing are in the corresponding one-letter code.

Alternatively, the AFP may be selected from the group consisting of fish AFPs (e.g., type I AFPs, type II AFPs, type III AFPs and type IV AFPs), plant AFPs and AFPs and antifreeze glycoproteins (AFGPs). For example, AFGPs and type I AFPs have an amino acid sequence of the formula $R^1$-(AA1-AA1-AA2)$_x$-$R^2$. Each AA1 is independently Ala, Asn, Gly, Val, Leu Pro, Phe, Thr, Tyr, or Ile, each AA2 is independently Thr or Ser or Tyr, $R^1$ is H, $C_{1-6}$ alkyl, $R^3$—C(=O)— or $R^3$—OC(=O)—, x is an integer of at least 3, $R^2$ is OH, $C_{1-6}$ alkoxy, $R^4$—NH— or $R^4{}_2$N—, $R^3$ is $C_{1-6}$ alkyl, $C_{6-10}$ aryl, or $C_{1-6}$ alkyl or $C_{6-10}$ aryl substituted with one or more halogen atoms and/or $C_{1-4}$ alkyl groups, and $R^4$ is $C_{1-4}$ alkyl. Type II and type III AFPs are independent globular proteins without significant repeat units. Type IV AFPs are four-α-helix bundle proteins. Alternatively, the fish AFP may be a type I AFP (SEQ ID NO. 16), a type II AFP (SEQ ID NO. 17, SEQ ID NO. 20), or a type III AFP (SEQ ID NO. 18, SEQ ID NO. 19).

Alternatively, the AFP may be selected from the group consisting of plant, bacteria, and fungi AFPs. For example, the plant AFP may be an AFP from *Lolium perenne* (SEQ ID NO. 21). In another example, the bacteria AFP may be an AFP from *Sulfitobacter* sp. (SEQ ID NO 22).

When the AFP is one or more of the AFPs or AFGPs having the amino acid sequence of the formula $R^1$-(AA1-AA1-AA2)$_x$-$R^2$, each AA1 may independently be Ala, Gly, Val, Leu, or Ile, and in some embodiments, the amino acid sequence may have the formula $R^1$-[Ala-Ala-Thr]$_x$-$R^2$, where 0-10% of the alanines in the formula $R^1$-[Ala-Ala-Thr]$_x$-$R^2$ are replaced with glycine or leucine and 0-10% of the threonines in the formula $R^1$-[Ala-Ala-Thr]$_x$-$R^2$ are replaced with serine or tyrosine. Furthermore, x may be 8-100, 10-60, or 30-50 and/or 10-12. The AFPs or AFGPs having the amino acid sequence of the formula $R^1$-(AA1-AA1-AA2)$_x$-$R^2$ may include one or more mono- or disaccharides (any of which may further include an acetylamido or other $C_{1-4}$ alkanoylamido groups in place of an OH group) linked to a threonine (or serine) hydroxyl group through a glycosidic linkage.

In further embodiments, the method may further comprise mixing the heated crude AFP. Mixing may comprise stirring (e.g., mechanically or magnetically), shaking (e.g., with a mechanical shaker or a vortex mixer), inverting, etc. Thus, the heated crude AFP may be mixed during or after heating the crude AFP. For example, the heated crude AFP may be mixed (e.g., during heating) at a rotational speed of 20-40 rpm. Alternatively, the heated crude AFP may be mixed by inverting a container or other vessel containing the crude AFPs.

In other or further embodiments, removing the precipitates may comprise centrifuging the heated crude AFP (which may be cooled prior to centrifuging) and decanting or filtering at least the supernatant. Alternatively, removing the precipitates may comprise filtering the heated crude AFP (which may be cooled prior to filtering). Some embodiments of the present method may further comprise adjusting a pH of the aqueous medium using a buffer solution, before heating the crude AFP.

In various embodiments of the method, the crude AFP includes a cell lysate of a recombinant or natural source of the AFP (e.g., the recombinant AFP source). In some examples, the recombinant source of the AFP may be a bacterium. In further embodiments, the recombinant AFP includes one or more tags configured to facilitate identification, purification, solubility and/or thermal resistance of the AFP. For example, the tag(s) may comprise an amino acid sequence or polypeptide that has or includes one or more unique properties or characteristics for identification, purification, or thermal stability of the AFP (e.g., the tag may enhance binding to a chromatography medium, a metal affinity resin, or a solid support to which an antibody is coupled; the tag may increase the temperature at which the AFP loses activity; etc.). At least one of the tags may be at an N- or C-terminus of the AFP, or is otherwise genetically grafted onto the recombinant AFP.

Alternatively, the crude AFP includes a fluid or extract from a plant, animal, bacterium, yeast or fungus that naturally accumulates the AFP. In some examples, the fluid or extract is from an animal (e.g., an insect or a fish).

The present method may further comprise purifying the AFP in the supernatant by liquid chromatography. For example, the AFP in the supernatant may have a purity of at least 85%, and after the liquid chromatography, the AFP may have a purity of at least 90%.

Another aspect of the present invention concerns a method of producing an antifreeze protein (AFP), comprising collecting a crude source of the AFP, and purifying the AFP by the present purification method. For example, collecting the crude source of the AFP may comprise growing or culturing a host configured to express a recombinant AFP in a growth medium. The growth medium may comprise water and a protein hydrolysate or other source of amino acids, and in further embodiments, may further comprise a yeast extract. The water may comprise deionized water and/or a buffer, and the protein hydrolysate or other source of amino acids may comprise tryptone or soytone. In various embodiments, the protein hydrolysate or other source of amino acids may be present in an amount providing a concentration of 1 to 40 g of the protein hydrolysate or other source of amino acids per liter of the growth medium. The yeast extract may be present in an amount providing a concentration of 1 to 50 g of the yeast extract per liter of the growth medium.

In other or further embodiments, the growth medium may further comprise a biologically metabolizable $C_3$-$C_6$ polyol (e.g., glycerol). For example, the biologically metabolizable $C_3$-$C_6$ polyol may be a liquid polyol and/or may be present in an amount providing a concentration of 0.1 to 10 ml of the liquid polyol per liter of the growth medium. Alternatively, the biologically metabolizable $C_3$-$C_6$ polyol may be a solid polyol and/or may be present in an amount providing a concentration of 0.1 to 10 g of the solid polyol per liter of the growth medium.

In the method of producing an AFP, the host may be a microbe (e.g., a bacterium), and the method may further comprise sterilizing the growth medium (e.g., before adding the microbe). The growth medium may be sterilized by autoclaving, filtration and/or irradiation. The method of producing an AFP may also further comprise inducing expression of the recombinant AFP.

In the method of producing an AFP, growing or culturing the host may comprise incubating the host. For example, the host may be incubated at a temperature of 10° C. to 50° C. and/or for a duration of time that is inversely proportional to the temperature.

The method of producing an AFP may further comprise harvesting the host by centrifugation and/or disrupting the host to obtain a crude cell extract. The host may be disrupted by a mechanical method or a chemical method (e.g., the mechanical method). For example, the mechanical method may include use of a French press. Alternatively, the host may be disrupted by the chemical method. The chemical method may include use of lysozyme.

The method of producing an AFP may further comprise centrifuging the crude cell extract to obtain a supernatant separated from a solid material, isolating or extracting the crude AFP from a plant, animal, bacterium, yeast or fungus that naturally accumulates the AFP. For example, the crude AFP may be isolated or extracted from a plant (e.g., a plant seedling) or, alternatively, from an animal (e.g., an insect or a fish). In some cases, the crude AFP may be isolated or extracted from insect larvae. In various embodiments, isolating or extracting the crude AFP may comprise collecting the plant, animal, bacterium, yeast or fungus from a natural source. In further embodiments, isolating or extracting the crude AFP may further comprise separating an organ, tissue or fluid in which the crude AFP accumulates from the plant, animal, bacterium, yeast or fungus, and then isolating or extracting the crude AFP from the organ, tissue or fluid.

Yet another aspect of the present invention concerns a method of producing an antifreeze protein (AFP), comprising growing or culturing a host configured to express a recombinant AFP in a growth medium, and collecting a crude AFP from the host and/or the growth medium. The growth medium comprises water, a protein hydrolysate or other source of amino acids, a yeast extract, a biologically metabolizable $C_3$-$C_6$ polyol, and one or more phosphate salts. The method may further comprise purifying the AFP by the present purification method.

As for other aspects of the invention, the water may comprise deionized water and/or a buffer, the protein hydrolysate or other source of amino acids may comprise tryptone or soytone, the biologically metabolizable $C_3$-$C_6$ polyol may comprise glycerol, the phosphate salt(s) may comprise mono- and/or di-basic potassium phosphate. The protein hydrolysate or other source of amino acids may be present in an amount providing a concentration of 1 to 40 g of the protein hydrolysate or other source of amino acids per liter of the growth medium, and the yeast extract may be present in an amount providing a concentration of 1 to 50 g of the yeast extract per liter of the growth medium.

In various embodiments, the biologically metabolizable $C_3$-$C_6$ polyol may be a liquid polyol, and may be present in an amount providing a concentration of 0.1 to 10 ml of the liquid polyol per liter of the growth medium. Alternatively, the biologically metabolizable $C_3$-$C_6$ polyol may be a solid polyol, and may be present in an amount providing a concentration of 0.1 to 10 g of the solid polyol per liter of the growth medium. The phosphate salt(s) may be present in an amount of from 5 to 25 g per liter of medium.

In some embodiments, the host may be grown or cultured at a temperature of from 10° C. to 50° C. and/or for a length of time of from 2 to 60 hours (e.g., from 2 to 44 hours or any other length of time or range of lengths of time therein, such as 2 to 24 hours).

The cost of manufacturing and/or producing AFPs has been a great concern when implementing commercial applications of AFPs. The methods and improvements described herein have great economic potential and will enable mass production of purified AFPs for the commercialization of AFPs. These and other advantages of the present invention will become readily apparent from the detailed description of various embodiments below.

DETAILED DESCRIPTION

Figure 1:
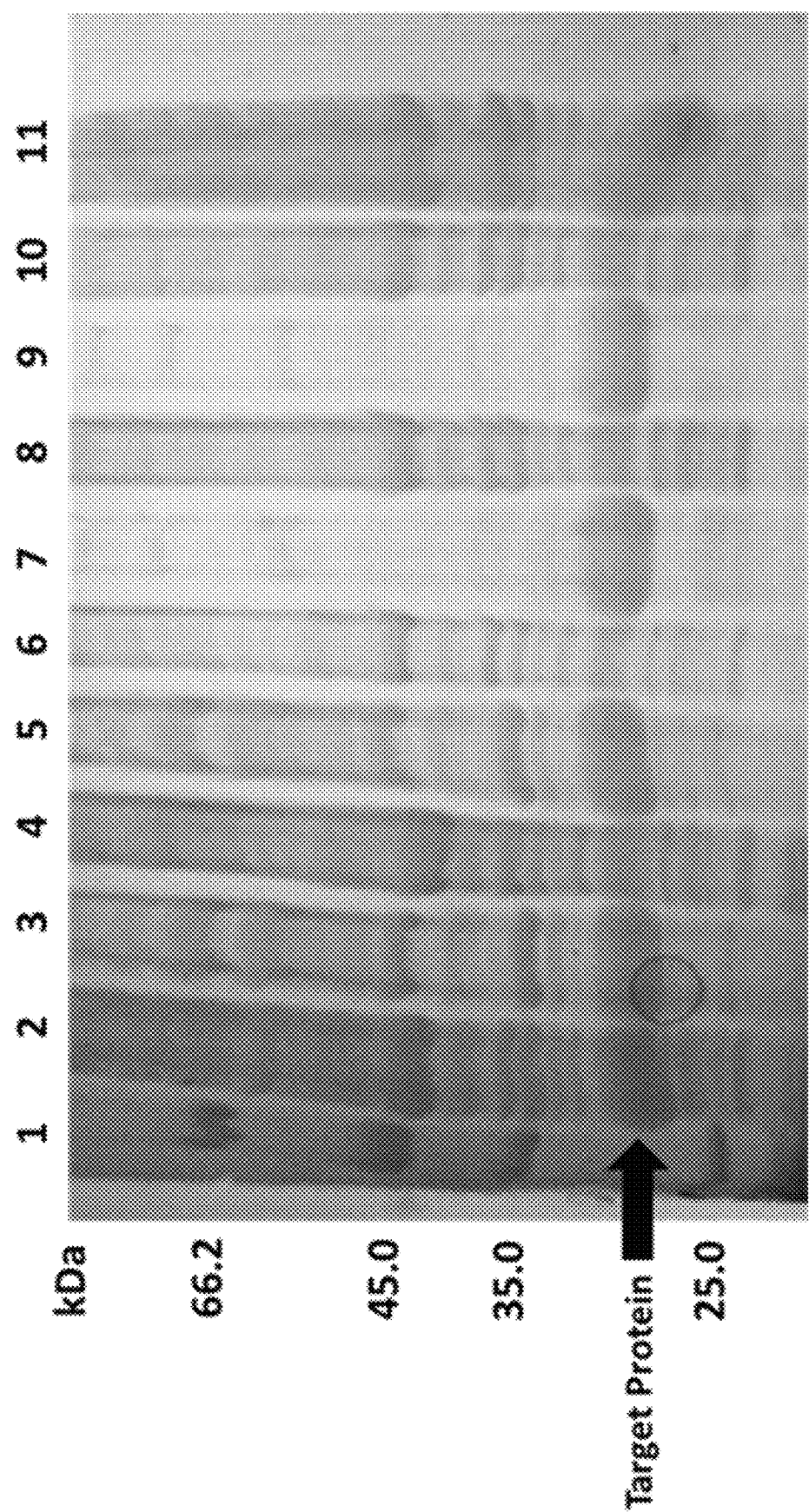
FIG. 1 shows an SD S-PAGE gel picture of the crude protein extraction after various heat purification treatments.

Reference will now be made in detail to various embodiments of the invention, examples of which are illustrated in the accompanying drawings. While the invention will be described in conjunction with the following embodiments, it will be understood that the descriptions are not intended to limit the invention to these embodiments. On the contrary, the invention is intended to cover alternatives, modifications and equivalents that may be included within the spirit and scope of the invention as defined by the appended claims. Furthermore, in the following detailed description, numerous specific details are set forth in order to provide a thorough understanding of the present invention. However, it will be readily apparent to one skilled in the art that the present invention may be practiced without these specific details. In other instances, well-known methods, procedures, components, and circuits have not been described in detail so as not to unnecessarily obscure aspects of the present invention.

The technical proposal(s) of embodiments of the present invention will be fully and clearly described in conjunction with the drawings in the following embodiments. It will be understood that the descriptions are not intended to limit the invention to these embodiments. Based on the described embodiments of the present invention, other embodiments can be obtained by one skilled in the art without creative contribution and are in the scope of legal protection given to the present invention.

Furthermore, all characteristics, measures or processes disclosed in this document, except characteristics and/or processes that are mutually exclusive, can be combined in any manner and in any combination possible. Any characteristic disclosed in the present specification, claims, Abstract and Figures can be replaced by other equivalent characteristics or characteristics with similar objectives, purposes and/or functions, unless specified otherwise.

The term "AFP" may defined herein as the cumulative group consisting of natural antifreeze proteins or antifreeze polypeptides or antifreeze peptides that are predominantly present or expressed in the organism (e.g., at a peak level) in winter; engineered antifreeze proteins, antifreeze polypeptides and antifreeze peptides based on the natural forms; active fragments of antifreeze proteins, antifreeze polypeptides and antifreeze peptides based on the natural forms; mimetics of antifreeze proteins, antifreeze polypeptides and antifreeze peptides based on the natural forms; their active mimetic fragments; analogs and homologs of antifreeze proteins, antifreeze polypeptides and antifreeze peptides based on the natural forms; and combinations thereof. For example, the AFP may be (i) encoded by a gene that is expressed in the corresponding natural organism at a peak level in winter (and, optionally, that is expressed at a relatively low level in summer), or (ii) an analog, active fragment or mimetic of such an AFP. The foregoing term "antifreeze" may be defined as having or providing one or more antifreeze properties or characteristics (e.g., thermal hysteresis, ice binding, ice structuring, inhibition of ice growth, inhibition of ice recrystallization), which may be a threshold level or value of the property or characteristic. The term "ice-like crystalline structures" may be defined as ice, gas hydrates and clathrate hydrates that are in the solid phase.

The present invention relates in part to an improved method for the purification and/or production of antifreeze proteins. The invention, in its various aspects, will be explained in greater detail below with regard to exemplary embodiments.

The improved expression method of recombinant AFPs includes the use of terrific broth medium or similar growth medium (which may be supplemented with tryptone, soytone, or another protein hydrolysate or source of amino acids) for production of AFPs using recombinant microbes. For example, the medium may include deionized water and/or a known buffer (e.g., a mono- and/or dibasic potassium phosphate buffer), yeast extract in an amount providing a concentration of 1 to 50 g/L in the medium, tryptone or other protein hydrolysate or source of amino acids in an amount providing a concentration of 1 to 40 g/L in the medium, and optionally, glycerol or other biologically metabolizable $C_3$-$C_6$ polyol in an amount providing a concentration of 0.1 to 10 ml/L (for a liquid polyol) or g/L (for a solid polyol) in the medium. The medium may be sterilized (e.g., by autoclaving at 120-125° C. for 10-30 min at 1-2 kg/cm$^2$ added pressure, or alternatively, by filtering and/or irradiating the medium in accordance with known techniques). Alternatively, the growth medium may contain a salt (e.g., sodium chloride) and/or a polysaccharide (e.g., agar) in respective amounts of from 10 to 250 g/L of the medium or 1 to 50 g/L of the medium.

There are problems in producing AFPs from their natural sources, such as sporadic or short supplies, and economic disadvantages. Consequently, fermentation (e.g., industrial fermentation) of microorganisms (both prokaryotic and eukaryotic), as well as eukaryotic cells, that include genes for expressing an AFP is advantageous for the production of AFPs in large amounts, especially as recombinant DNA technology progresses.

Prokaryotic and eukaryotic microorganisms, such as bacteria, cyanobacteria, fungi, algae, protozoa, and yeast, can be used for industrial fermentation. Eukaryotic cells, such as yeasts, mammalian cells, and insect cells, are currently used for industrial fermentation. For example, AFPs can be cloned and expressed in non-methylotrophic yeasts (e.g., *Saccharomyces cerevisiae* and the species or strain *Yarrowia lipolytica*), methylotrophic yeasts (e.g., *Pichia pastoris* and the species or strain *Hansenula polymorpha*), and Chinese hamster ovary (CHO) cells, using a Baculovirus expression system, an HEK293 expression system, or an Expi293 expression system. More specifically, genes encoding AFPs from the beetle *Dendroides canadensis* (dafps) have been subcloned and expressed in *Escherichia coli* using a bacteria expression system (Wang et al., *Biochemistry*, vol. 30 [2005], pp. 10305-10312), and genes of insect AFPs from the spruce budworm (*Choristoneura fumiferana*) and yellow mealworm (*Tenebrio molitor*) have been expressed in *Pichia pastoris* using a yeast expression system (Tyshenko et al., *Protein Expression and Purification*, vol. 47 [2006], pp. 152-161).

For example, rAFPs from *Dendroides canadensis* (DAFPs) can be prepared as described in Wang et al., *Biochemistry*, vol. 30 [2005], pp. 10305-10312, Amornwittawat et al., "Polycarboxylates Enhance Beetle Antifreeze Protein Activity," *Biochim. Biophys. Acta,* 1784:1942-1948 (2008) or Wang et al., *Biochemistry*, vol. 48 (2009), pp. 9696-9703. The recombinant meal worm *Tenebrio molitor* AFP (TmAFP) can be prepared using procedures described in Bar et al., *Protein Expression and Purification*, vol. 48 (2006), pp. 243-252, or Zamalloa, Master's Thesis, Dept. of Chemistry, California State University-Los Angeles (2012). Alternatively, the recombinant insect AFPs can be prepared as described in Tyshenko et al., *Protein Expression and Purification*, vol. 47 (2006), pp. 152-161. The recombinant fish Type III can be prepared using procedures described in Kuiper et al., *Biochemical and Biophysical Research Communications*, vol. 300 (2003) pp. 645-648.

The purification method described herein may include obtaining a crude source of AFPs, heating the crude source of AFPs to 45-85° C. (e.g., 60-70° C.) for 5 min to 4 hours (e.g., 10 min-2 h), optionally mixing the heated crude source of AFPs (which may be a solution), and removing any precipitates that form during heating. Examples of crude sources of AFPs include a cell lysate (e.g., the water-soluble part of a cell lysate) of a recombinant or natural source of AFPs (e.g., bacteria, yeasts, plants, insects, fish, etc.), and fluids or extracts from plants, animals, or fungi that naturally accumulate AFPs. The pH may be adjusted using a buffer solution before raising the temperature. The heated crude AFPs may be mixed at a rotational speed of, e.g., 20-40 rpm, or by inverting the container containing the crude AFPs. Precipitates may form during the heating. Consequently, after the heating step, the precipitates may be removed by centrifugation and/or filtering. The purified AFPs (>85%) are in the supernatant. Careful adjustment of the pH of the crude solution prior to heat treatment can improve the purity of the AFPs achieved after the heat treatment. Alternatively or additionally, the purity of the AFPs can be further improved to 95% or higher by an additional chromatography step. For example, affinity chromatography, ion exchange chromatography (either anion exchange or cation exchange chromatography), or size-exclusion (i.e., gel filtration) chromatography may be used. Furthermore, if complete removal of a fusion domain (or tag) that attaches to the protein is necessary, the specific procedure(s) to remove the tag (e.g., enzymatic cleavage of the fusion tag and then removal of the tag) may be carried out after the heat treatment. One significant benefit of the present purification method is that, as a result of precipitating thermally unstable proteins, the viscosity of the lysed cell solution or suspension is much smaller than that of similar or otherwise identical cell lysate solutions or suspensions that are not heated to a temperature of 45° C. or more (e.g., 60° C. or more) during purification).

The host or other source of crude AFPs may be selected so that there is little or no significant amount of other thermally stable proteins in the cell supernatant at the temperature of the heat treatment. For example, the AFP may be produced in a recombinant host (such as $E.\ coli$ cells or eukaryotic cells) that does not produce an appreciable amount of thermally stable proteins in the absence of the recombinant gene that expresses the AFP(s).

In some examples, the recombinant AFP may include one or more known tags configured to facilitate identification, purification, solubility and/or thermal resistance of the AFP. As used herein, a "tag" may refer to an amino acid sequence or polypeptide (typically at an N- or C-terminus of the AFP, or that is otherwise genetically grafted onto the recombinant AFP) that has or includes one or more unique properties or characteristics for identification (e.g., by fluorescence or other spectroscopy [e.g., UV-Vis spectroscopy] at a particular wavelength of IR or UV light), for purification (e.g., by binding or not binding to or chromatography medium such as an ion-exchange resin or a solid support to which an antibody is coupled), or for thermal stability (e.g., by increasing the temperature at which the AFP loses appreciable or significant activity). Alternatively, the tag may facilitate expression and/or purification from the crude recombinant AFP source using an affinity technique. Such affinity tags include chitin binding protein (CBP), maltose binding protein (MBP), streptavidin- and streptactin-binding tags, glutathione-S-transferase (GST), and poly(His) (which binds to a metal matrix, such as nickel-nitrilotriacetic acid [Ni-NTA]). Solubilization tags include thioredoxin (TRX) and poly(NANP). The affinity tags MBP and GST may also function as solubilization tags. The effect of such tags on the thermal stability of a tagged protein is not fully understood. Different tags may have different effects on different classes of the tagged proteins, and even the same tag may have different effects on the thermal stability of different classes of proteins. In some embodiments of the present invention, the tag is one that enhances, or at least does not impede or adversely affect, the thermal stability of the tagged protein. However, to the best of the inventor's knowledge, the thermal stability of tagged AFPs has not yet been studied.

An AFP tagged with cleavable TRX-, S-, and His-tags was expressed in $E.\ coli$, and the present heat treatment was applied to the supernatant having the tagged AFP therein. The total size of the tags was about 17 kDa. Depending on the application for which the AFP is to be used, the tag may or may not be cut, cleaved or removed. However, purification of rAFPs using the present heat-treatment method has been successful experimentally, both when the rAFP contains a tag and after the tag is removed.

The yield of the AFP, both tagged and tag-free, provided by the present invention is significantly greater (at least 30% greater) than prior methods (e.g., recombinant expression and purification by multiple chromatography passes, without heat treatment). The purity of the AFP produced using the present invention is similar to or higher than a single chromatography pass, although the purity may be comparable to multiple chromatography passes. However, when multiple chromatography passes are used, the yield is significantly lower and the process time is significantly longer than that provided by the present invention.

In various embodiments, the present method can be used to produce AFPs such as DAFPs and DAFP mutants, as well as other antifreeze proteins including fish AFPs and other insect AFPs (e.g., TmAFPs) and their mutants. DAFPs and TmAFPs are hyperactive AFPs (e.g., having a relatively high thermal hysteresis value). Both DAFPs and TmAFPs have a β-helical (i.e., β-solenoid) structure and share high sequence identities (>40%) and high sequence similarities (>60%). Despite their different structures, the present inventor has found that Types II and III fish AFPs, fish AFGPs, and recombinant DAFPs and TmAFPs and their mutants are generally thermally stable.

In further embodiments, some fish AFPs, such as Type I AFPs and AFGPs comprising or consisting of repeated Ala-Ala-Thr units (e.g., having the formula $R^1$-[Ala-Ala-Thr]$_x$-$R^2$, where $R^1$ is H, $C_{1-6}$ alkyl, $R^3$—C(=O)— or $R^3$—OC(=O)—, x is an integer of at least 3 [e.g., 8-100, 10-50, or any value or range of values therein], $R^2$ is OH, $C_{1-6}$ alkoxy, $R^4$—NH— or $R^4_2$N—, $R^3$ is $C_{1-6}$ alkyl, $C_{6-10}$ aryl, or $C_{1-6}$ alkyl or $C_{6-10}$ aryl substituted with one or more halogen atoms (e.g., F or Cl) and/or $C_{1-4}$ alkyl groups, and $R^4$ is $C_{1-4}$ alkyl), may also be effective in the present invention. Furthermore, other amino acids with similar physical and/or chemical properties may be substituted for one or more of the alanines or threonines in one or more of the units. Accordingly, these fish AFP isoforms suitable for use in the present method and composition include those having the formula $R^1$-(AA1-AA1-AA2)$_x$-$R^2$. Each AA1 is independently Ala, Asn, Gly, Val, Leu Pro, Phe, Thr, Tyr, or Ile, each AA2 is independently Thr or Ser or Tyr, and $R^1$ and $R^2$ are as described above. In some examples, no more than 10% of the alanines or threonines in the formula $R^1$-[Ala-Ala-Thr]$_x$-$R^2$ are replaced with a different amino acid (e.g., Ala replaced with Gly and/or Thr replaced with Ser). The present fish AFPs and isoforms thereof may be glycosylated (e.g., with one or more β-d-galactosyl(1→3)-α-N-acetylgalactosamine or other mono- or disaccharide [any of which may include an acetylamido or other $C_{1-4}$ alkanoylamido groups in place of an OH group] linked to the AA2 hydroxyl group through a glycosidic linkage.

The AFP may also be selected from other fish AFPs and AFGPs (e.g., type I-IV AFPs and AFGPs), plant AFPs, bacterial AFPs, and fungus AFPs that are present or expressed predominantly in winter. Type I AFPs include an alanine-rich α-helix. Type II AFPs and type III AFPs are unrelated globular proteins having no repetitive characters (e.g., amino acid sequences). Type II AFPs have a lectin-like fold with mixed α, β, and loop structures, while type III AFPs shows a compact fold with short and/or irregular β-strands. AFGPs are glycoproteins, and may adopt a polyproline II structure.

Both O-linked and C-linked analogs of antifreeze glycoproteins have been prepared. Antifreeze protein, glycoprotein, polypeptide and peptide analogs may also include those disclosed in U.S. Pat. No. 9,394,327, the relevant portions of which are incorporated herein by reference, and antifreeze peptoids and polymers such as those disclosed in International Pat. Publ. No. WO 2017/066454 and in Mitchell, D. E., et al., "Antifreeze Protein Mimetic Metallohelices with Potent Ice Recrystallization Inhibition Activity," *J. Am. Chem. Soc.* (2017) 139:29, 9835-9838, the relevant portions of which are incorporated herein by reference. The AFP, AFP analog, or AFP mimetic inhibits or controls crystallization of the carbohydrate (e.g., during the storage of the solution of the carbohydrate or the analog thereof, during the freeze-drying of a formulation using the carbohydrate or the analog thereof) and stabilizes a solution or formulation including the carbohydrate or the carbohydrate analog.

Despite their different structures, the AFPs and AFGPs are thought to have a relatively flat region or surface in their structures. These relatively flat surfaces of AFPs may help the AFPs to fulfill one of their original evolutionary functions (e.g., recognizing specific surfaces of ice crystals in order to halt their propagation).

Type I AFPs can be found in fish such as winter flounder, longhorn sculpin and shorthorn sculpin. Its three-dimensional structure has been determined. Type I AFPs generally consist of a single, long, amphipathic alpha helix, about 3.3-4.5 kDa in size. There are three faces to the 3D structure: the hydrophobic, hydrophilic, and Thr-Asx faces (see, e.g., FIG. 1). Type III AFPs exhibit similar overall hydrophobicity at ice binding surfaces to type I AFPs. They are approximately 6 kD in size. One type III AFP is fish AFP III, a prototypical globular AFP having size (or molecular mass) of 7 kDa that is present in members of the fish subclass Zoarcoidei.

In the AFP analogs and homologs, the mutations or differences may not be in amino acids known to be essential for activity of the (poly)peptide. Preferably any differences in the amino acid sequence of an AFP analog or homolog are silent mutations, whereby the substitutions are conservative substitutions that do not alter the hydropathy profile of the polypeptide and thus presumably do not severely influence the polypeptide structure and the activity. For example, an amino acid with a hydrophobic side chain is preferably exchanged only with another amino acid with a hydrophobic side chain, and an amino acid with a hydrophilic side chain is preferably exchanged only with another amino acid with a hydrophilic side chain.

An amino acid sequence exhibiting homology above 40%, preferably more than 60%, and most preferably more than 70% (or any percentage greater than 70% but less than 100%) can be expected to be representative of a polypeptide exhibiting similar properties to a natural AFP (Qin et al., *Tenebrio molitor* antifreeze protein gene identification and regulation, *Gene* (2006) 367:142-149). In addition, the polypeptide encoded by the amino acid sequence should exhibit at least 40% (or any percentage greater than 40%) of the AFP activity of native AFP.

Activity of recombinant AFPs, engineered AFPs, antifreeze polypeptides and antifreeze peptides, active fragments of AFPs, antifreeze polypeptides and antifreeze peptides, mimetics of AFPs, antifreeze polypeptides and antifreeze peptides, their active mimetic fragments, AFP analogs and homologs, and combinations thereof can be determined by carrying out comparisons with ice affinity, thermal hysteresis (TH) measurements, or recrystallization assays using a series of dilutions of the polypeptide and equal amounts and dilutions of AFPs as obtained from natural sources. The manner in which the characteristics and/or properties in ice binding, TH, and ice recrystallization can be carried out and evaluated is known in the art.

EXPERIMENTAL SECTION

Example 1

Unless mentioned otherwise, all chemicals and reagents can be obtained from Sigma-Aldrich (St. Louis, Mo., USA). All solutions can be prepared using Milli-Q water produced from a Synergy water system (Millipore Co.) with a minimum resistivity of 18 MΩ·cm.

Bacterial cells (e.g., *E. coli* Origami B) harboring a recombinant AFP (rAFP) gene (e.g., pET32b-DAFP-1) were grown in microbial media (e.g., Luria-Bertani medium) supplemented with antibiotics (e.g., 15 μg/mL kanamycin and 50 μg/mL ampicillin).

When the gene is under the control of the lac operator, isopropyl-1-thio-β-D-galactopyranoside (IPTG) is added to the medium to trigger transcription of the lac operon and thus to induce the protein expression. The final concentration of IPTG is within the range of 0.05-1.0 mM. Alternatively, an autoinduction expression system can be used. The microbe/culture is then incubated. The duration of the incubation depends on the temperature. For example, the duration of the incubation can be from 12 to 30 hours at 15° C., 6 to 16 hours at room temperature, 3 to 6 hours at 37° C., etc. Alternatively, the concentration of a compound in the microbial medium that is consumed during growth of the microbe and/or production of the AFP can be monitored, and the cells can be harvested when the concentration of the compound falls below a predetermined threshold. After incubation of the culture, the cells were harvested by centrifugation.

The cells were then lysed by a physical disruption method and/or a chemical method to obtain a crude cell extract. Mechanical methods include use of a French press (Thermo Fisher), a sonicator, or freeze-thaw. Chemical methods include use of lysozyme. The crude cell extract was then centrifuged to separate the supernatant from solid pellets.

More specifically, *E. coli* Origami B cells harboring pET32b-DAFP-1, -2, -4, -6 or TmAFP4-9 can be briefly grown in lysogeny broth (LB) media supplemented with kanamycin (15-30 μg/mL) and ampicillin (50-100 μg/mL). Isopropyl β-D-1-thiogalactopyranoside (IPTG) (0.5-1.0 mM) is added to the culture to induce a high-level expression of AFPs when OD600 (absorbance at 600 nm) reaches 0.6. The cells (whether grown in LB or Luria-Bertani medium) can be harvested by centrifugation at 4° C. The cells are resuspended into a lysis buffer with a pH about 0.5 unit away from the pI of the target protein, and then are disrupted, for example, using lysozyme (Sigma-Aldrich) or by two passes through a French press (Thermo Fisher).

Heat shock was applied to the portion of the crude cell extract that includes the majority of the target protein (i.e., the supernatant resulting from removal of the cell debris or pellets, usually by centrifugation, after disruption). The cell extract can be from cells obtained from any of a wide volume range of culture media (e.g., about 0.2-40 liters). The volume of the crude cell extract can range from milliliter- to liter-scale (e.g., from about 10 mL to about 2 liter). The volume of the crude cell extract may be aliquoted into smaller uniform volumes for efficient heat treatment. The temperature of the supernatant from the crude cell extract (i.e., the source of the rAFP) was raised to a temperature of 50-80° C. (e.g., 70° C.) and incubated at that temperature for a certain time duration of from 5 min to 60 min (e.g., 10 min). During the incubation, the sample may be mixed occasionally by inverting the vessel containing the sample or shaking the vessel gently to help the heat transduction throughout the sample. Alternatively, heat shock can be applied directly to the lysed cell solution after cell lysis without removing the cell debris/pellets.

After heat incubation, the sample was centrifuged to remove any precipitate caused by the heat shock. The heat-treated supernatant contains purified rAFP (>85%). Thereafter, the buffer can be changed so that the purified rAFP can be used in subsequent applications (e.g., cryopreservation, preventing or controlling crystallization of a sugar or nucleoside, thermal protection of a non-AFP protein, cell component, cell, tissue or organism, etc.).

FIG. 1 shows an SDS-PAGE gel picture of the crude protein extraction after various heat purification treatments. Lanes 1, 2, and 11 are protein marker, crude extract supernatant, and pellet without heat treatment. Lanes 3-6 are the samples after treatment at 50° C. [lane 3: supernatant after 30 min heat treatment, lane 4: pellet after 30 min heat treatment; lane 5: supernatant after 45 min heat treatment, lane 6: pellet after 45 min heat treatment]. Lanes 7-10 are the samples after treatment at 70° C. (lane 7: supernatant after 15 min heat treatment, lane 8: pellet after 15 min heat treatment; lane 9: supernatant after 30 min heat treatment, lane 10: pellet after 30 min heat treatment). The rAFP (at about 26 kDa) is designated with the large arrow. Impurities are at sizes greater or smaller than that of the target protein, about 26 kDa). Lanes 3 and 5 show significant purification of the rAFP relative to the crude supernatant (lane 2). Lanes 7 and 9 (70° C. treatment) show very little impurity in the heat-treated rAFP.

The resulting supernatant is clear and much less viscous than the supernatant of the non-treated crude cell extract. To increase the AFP purity (e.g., to >95%), the treated supernatant can be further purified by chromatography. The greatly reduced viscosity of the heat-treated (and purified) AFP solution saves appreciable time during subsequent chromatography.

For example, the crude protein may be further purified using nickel-nitrilotriacetic-acid (Ni-NTA) agarose, if needed. The terminal tag (containing a hexahistidine unit) can be cleaved using enterokinase (e.g., Genscript) and removed using Ni-NTA agarose (e.g., Qiagen). The cleaved protein can then be further purified using an AKTA Purifier 10 (GE Healthcare) equipped with a Sephacryl S-100 gel filtration column (GE Healthcare). The AFP concentration can be determined by UV-Vis spectroscopy using an absorption at 280 nm.

Example 2

The expression of recombinant AFPs is generally in a nutritionally rich medium, such as lysogeny broth (LB). By replacing chlorides (e.g., sodium chloride) with phosphates (e.g., mono- and/or di-basic potassium phosphate), and supplying glycerol and/or additional amounts of amino acids and/or yeast extract in the media, the expression time can be reduced to about 50% of the time for expressing the same rAFP in the same bacterial host in the same, unmodified medium (e.g., LB medium). In a specific case, the expression of rAFPs in a host bacterium grown in a terrific broth (TB) medium reduced the expression time to within 20 hours, even at a growth temperature 10° C. below ambient temperature. By contrast, the expression time for the same bacterium expressing the same rAFP in LB media was about 2 days at the same temperature. The crude cell extract of the cells grown in TB medium has been purified using the present heat shock method. In fact, the high viscosity of the cell extract of the cells grown in TB medium can be greatly reduced by applying the heat treatment method.

Test Example 1

The rAFPs in the test example were expressed as described in Example 1 above, the tag was removed, and the rAFPs were analyzed using the procedures described in Amornwittawat et al., Biochim. Biophys. Acta, 1784:1942-1948 (2008) and Rodriguez et al., International Journal of Biological Macromolecules, vol. 136, 1153-1160. Some of the rAFPs were purified using the heat shock method described in Example 1 above. More particularly, the terminal hexahistidine tag was cleaved from both heat-purified rAFPs and regularly-prepared rAFPs (i.e., rAFPs not subject to the present thermal purification) using enterokinase (e.g., Genscript), and then the cleaved tag was removed using Ni-NTA agarose chromatography (e.g., Qiagen).

More specifically, E. coli Origami B cells harboring pET32b-DAFP-1 were grown in lysogeny broth (LB) media supplemented with kanamycin (15 μg/mL) and ampicillin (50 μg/mL). IPTG (0.5 mM) was added to the culture to induce a high-level expression of AFPs when OD600 reached 0.6. The cells were harvested by centrifugation at 4° C. The cells were lysed using lysozyme (e.g., 0.1 mg/mL) in a lysis buffer (e.g., 50 mM Tris, pH 8.0, with EDTA-free protease inhibitor cocktail).

Figure 2:
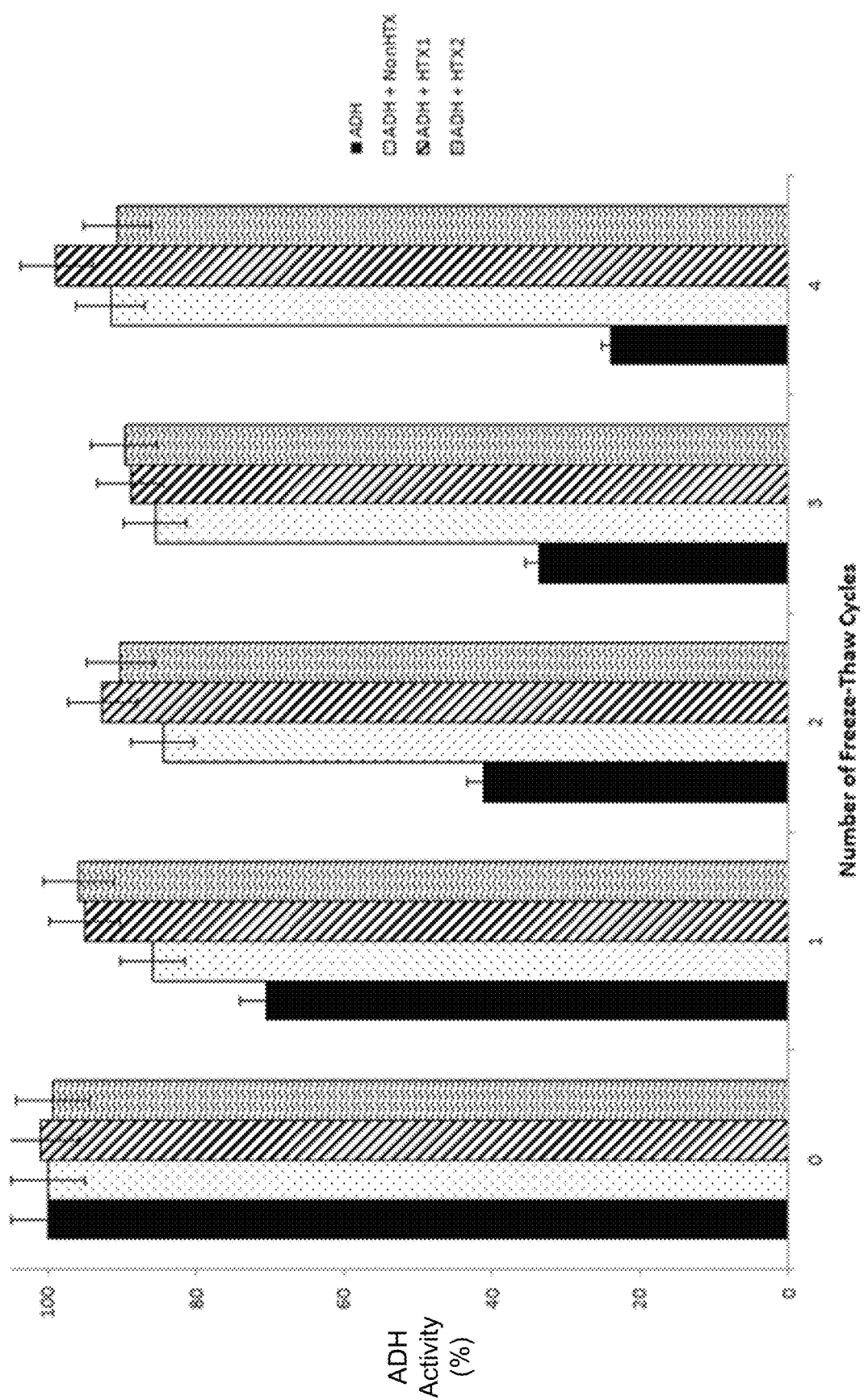
FIG. 2 is a graph showing the protective effect of a rAFP (DAFP-1) on the enzymatic activity of alcohol dehydrogenase (ADH) after one-four freeze-thaw cycles and without any freeze-thaw cycles, in comparison to that of ADH alone.

For "heat-purified" rAFP samples, such as "HTX1" and "HTX2" in FIG. 2, the cell lysates were heated at a predetermined temperature for a predetermined time period. Specifically, samples "HTX1" and "HTX2" (FIG. 2) were heated at 60° C. for 30 min and at 70° C. for 15 min, respectively. Thereafter, the heat-treated cell lysates were centrifuged at 12,000-15,000 rpm for at least about 15 min at room temperature or less (e.g., 4° C.) to separate the precipitates. The supernatant, which contained the tagged rAFP (typically at a purity of 85% or above), was separated (e.g., by decantation) and was ready for tag cleavage as described below.

For "regularly-prepared" rAFP (i.e., the sample[s] not subject to thermal purification or heat treatment; i.e., "Non-HTX" in FIG. 2), the cell lysates were also centrifuged at 12,000-15,000 rpm for at least about 15 min at room temperature or less (e.g., 4° C.) to separate the precipitates. The supernatant containing the tagged rAFP was purified by immobilized metal affinity chromatography (IMAC). For example, the supernatant containing the tagged rAFP was contacted with a nickel or cobalt-charged (e.g., nickel-nitrilotriacetic acid [Ni-NTA] or cobalt-iminodiacetic acid [Co-IDA]) affinity resin or agarose. The tagged rAFP has a His-tag, and thus has a high affinity to the nickel or cobalt-charged agarose resin. The tagged rAFP was eluted using an elution buffer (e.g., 50 mM Tris, 300 mM NaCl, and imidazole at a concentration from about 80-500 mM, pH 8.0). If the purity of the tagged rAFP after the affinity chromatography is below 85%, a further affinity chromatography step can further purify the tagged protein before the tag cleavage step described below.

The tagged proteins were purified, either by heat treatment or by affinity chromatography (i.e., as described in above), then subjected to tag removal, respectively. That is, the tagged rAFPs were incubated with enterokinase (His-tagged) in a cleavage buffer (e.g., 20 mM Tris-HCl, pH 7.4, 50 mM NaCl, and ideally with 2 mM $CaCl_2$) for about 16 hours at room temperature. Then, IMAC was used to remove the impurities (e.g., the cleaved tag, tagged rAFPs, and enterokinase) from the tag-free rAFPs. The tag-free rAFPs were used in the test below.

Heat-purified rAFPs show similar or better function/activity than otherwise identical rAFPs purified by chromatography alone. DAFPs can effectively protect a model freeze-labile enzyme under repeated freezing and thawing treatments (Rodriguez et al., *International Journal of Biological Macromolecules*, vol. 136, 1153-1160). The protective effect of rAFP on the enzymatic activity of another freeze-labile enzyme, alcohol dehydrogenases (ADH), under four repeated freezing-thawing treatments (i.e., freeze at −20° C. for an hour and thaw for four times) was tested. The assay follows the protocol published at https://www.sigmaaldrich.com/technical-documents/protocols/biology/enzymatic-assay-of-alcohol-dehydrogenase.html. The freeze-thaw experiments were performed in triplicate for each ADH sample. In general, heat-purified rAFPs show a similar or better protective effect on the enzymatic activity of ADH than that of rAFPs purified using only chromatography (FIG. 2).

FIG. 2 is a graph showing the protective effect of a rAFP (DAFP-1) on the enzymatic activity of alcohol dehydrogenase (ADH) after one-four freeze-thaw cycles and without any freeze-thaw cycles. Each freeze-thaw cycle included freezing at −20° C. for an hour, then thawing (e.g., warming the sample to room temperature). FIG. 2 shows the activity of the ADH enzyme in the absence of any additives ("ADH" in the legend in the right-hand side of FIG. 2) and in the presence of the rAFP purified by heat treatment at 60° C. for 30 min ("HTX1" in the FIG. 2 legend), the rAFP purified by heat treatment at 70° C. for 15 min ("HTX2" in the FIG. 2 legend), and the rAFP not subject to purification by heat treatment. The concentration of ADH in all samples is 200 µg/mL. The concentration of rAFP is the samples is 500 µg/mL. The freeze-thaw experiments were performed in triplicate for each sample.

The results in FIG. 2 show that, in the absence of the rAFP, ADH steadily loses its activity with repeated freeze-thaw cycles. However, in the presence of the rAFP, ADH retains most of its activity after 1-4 freeze-thaw cycles. The rAFP purified by the present heat shock method shows similar or perhaps marginally better activity than an equal amount of the same rAFP purified by chromatography alone, without the present heat shock method. Also, because the present heat shock purification process reduces the viscosity of the cell-lysed solution and the impurity level of the cell extract, the time for any subsequent chromatography process is reduced. For example, the reduced viscosity of the cell-lysed solution reduces the time of centrifugation, filtration, passing the solution through a membrane, and/or running a column, and can reduce the number of columns (or the number of times that the rAFP-containing solution is run through a column) for achieving a desired or predetermined purity level.

CONCLUSION/SUMMARY

The present purification method provides AFPs in purities and/or yields similar to or better than methods for preparing and purifying the same AFPs that include identical mechanical or chemical lysing procedures, but without thermal incubation or other heat treatment. Various rAFPs can be produced and purified using a wide variety of various parameter values, demonstrating that various expression and purification conditions work, and shorter incubation periods can be employed at higher temperatures. This method may also be used to improve the purification process of an unstable protein that has a chemical linkage to an AFP (e.g., a covalent bond to the AFP, in which the AFP also provides a thermal protection function to the unstable protein and prevents the unstable protein from losing some or all of its activity or function).

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

The invention claimed is:

1. A method of purifying an antifreeze protein (AFP), comprising:

heating a crude AFP in an aqueous medium to a temperature and for a length of time sufficient to precipitate at least some thermally unstable proteins in the crude AFP and form a precipitate and a supernatant, wherein the AFP is an AFP from *Dendroides canadensis* (DAFP), or a DAFP isoform or analog having an amino acid sequence of the formula A-(Thr-X-Thr-Y)$_z$-B, where A is a sequence of 8-12 amino acids, X is a sequence of from 1 to 3 amino acids, Y is a sequence of 1-12 amino acids, z is an integer of from 3 to 8, and B is a sequence of 1-5 amino acids; and removing the precipitate from the supernatant, wherein the AFP in the supernatant has a purity of at least 85%.

2. The method of claim 1, wherein the temperature is 45-90° C. and the length of time is 2 min to 4 hours.

3. The method of claim 2, wherein the temperature is 60-70° C. and the length of time is 10 min to 2 hours.

4. The method of claim 1, wherein removing the precipitates comprises centrifuging the heated crude AFP and decanting or filtering at least the supernatant.

5. The method of claim 1, wherein removing the precipitate comprises filtering the heated crude AFP.

6. The method of claim 1, wherein the crude AFP includes a cell lysate of a recombinant source of the AFP.

7. The method of claim 1, further comprising adjusting a pH of the aqueous medium using a buffer solution, before heating the crude AFP.

8. The method of claim 1, further comprising purifying the AFP in the supernatant by liquid chromatography, wherein the AFP has a purity of at least 90% after the liquid chromatography.

9. The method of claim 1, wherein the AFP is selected from the group consisting of DAFP-1 (SEQ ID NO 1), DAFP-2 (SEQ ID NO 2), DAFP-4 (SEQ ID NO 3), DAFP-6 (SEQ ID NO 4), DAFP-3 (SEQ ID NO 5), DAFP-5 (SEQ ID NO 6), DAFP-8 (SEQ ID NO 7), DAFP-11 (SEQ ID NO 8), and DAFP-13 (SEQ ID NO 9).

10. The method of claim 1, wherein A is Gln-Cys-Thr-Gly-Gly-Ser-Asp-Cys-Ser-Ser-Cys, X includes Cys, B is Gly-Cys-Pro, and z is 5 or 6.

11. The method of claim 1, wherein the temperature is 60-70° C.

12. A method of producing an antifreeze protein (AFP), comprising:
    collecting a crude source of the AFP; and
    purifying the AFP by the method of claim 1.

13. The method of claim 12, wherein collecting the crude source of the AFP comprises growing or culturing a host configured to express a recombinant AFP in a growth medium that comprises water, a yeast extract and a biologically metabolizable $C_3$-$C_6$ polyol and a protein hydrolysate or other source of amino acids.

14. The method of claim 13, wherein the water comprises deionized water and/or a buffer, and the protein hydrolysate or other source of amino acids comprises tryptone or soytone.

15. The method of claim 13, wherein the host is a bacterium.

16. The method of claim 13, further comprising disrupting the host to obtain a crude cell extract.

17. The method of claim 16, further comprising centrifuging the crude cell extract to obtain a crude supernatant containing the crude AFP, separated from a solid material.

18. A method of producing an antifreeze protein (AFP), comprising:
    growing or culturing a bacterial host configured to express a recombinant insect AFP in a growth medium, wherein the growth medium comprises water, a protein hydrolysate, a yeast extract, a biologically metabolizable $C_3$-$C_6$ polyol, and one or more phosphate salts, wherein the recombinant insect AFP is an AFP from *Dendroides canadensis* (DAFP) or an isoform or analog thereof having an amino acid sequence of the formula A-(Thr-X-Thr-Y)$_z$-B, where A is a sequence of 8-12 amino acids, X is a sequence of from 1 to 3 amino acids, Y is a sequence of 1-12 amino acids, z is an integer of from 3 to 8, and B is a sequence of 1-5 amino acids;
    collecting a crude insect AFP from the bacterial host and/or the growth medium;
    heating the crude insect AFP in an aqueous medium to a temperature and for a length of time sufficient to precipitate at least some thermally unstable proteins in the crude insect AFP and form a precipitate and a supernatant; and
    removing the precipitate from the supernatant.

19. The method of claim 18, wherein the temperature is 45-90° C. and the length of time is 2 min to 4 hours.

20. The method of claim 18, wherein the recombinant insect AFP is selected from the group consisting of DAFP-1 (SEQ ID NO 1), DAFP-2 (SEQ ID NO 2), DAFP-4 (SEQ ID NO 3), DAFP-6 (SEQ ID NO 4), DAFP-3 (SEQ ID NO 5), DAFP-5 (SEQ ID NO 6), DAFP-8 (SEQ ID NO 7), DAFP-11 (SEQ ID NO 8), and DAFP-13 (SEQ ID NO 9).

* * * * *